United States Patent
Kormann et al.

(10) Patent No.: US 7,372,034 B2
(45) Date of Patent: May 13, 2008

(54) AGRICULTURAL MEASUREMENT DEVICE WITH MOVABLE DETECTOR HEAD

(75) Inventors: Georg Kormann, Zweibrücken-Mörsbach (DE); Werner Flohr, Kaiserslautern-Dansenberg (DE)

(73) Assignee: Deere & Company, Moline, IL (US)

( * ) Notice: Subject to any disclaimer, the term of this patent is extended or adjusted under 35 U.S.C. 154(b) by 263 days.

(21) Appl. No.: 11/179,089

(22) Filed: Jul. 12, 2005

(65) Prior Publication Data
US 2006/0027750 A1  Feb. 9, 2006

(30) Foreign Application Priority Data
Aug. 7, 2004  (DE) ............... 10 2004 038 408

(51) Int. Cl.
*G01J 5/02*  (2006.01)
(52) U.S. Cl. ............ 250/341.8; 250/339.11; 56/10.1
(58) Field of Classification Search ........ 250/341.8
See application file for complete search history.

(56) References Cited

U.S. PATENT DOCUMENTS

| | | | | | |
|---|---|---|---|---|---|
| 4,742,228 | A | * | 5/1988 | Bischoff | 250/341.1 |
| 6,100,526 | A | * | 8/2000 | Mayes | 250/339.11 |
| 6,791,683 | B2 | * | 9/2004 | Sjodin | 356/326 |
| 6,845,326 | B1 | * | 1/2005 | Panigrahi et al. | 702/22 |
| 7,145,145 | B2 | * | 12/2006 | Benson | 250/339.07 |

FOREIGN PATENT DOCUMENTS

| | | |
|---|---|---|
| DE | 196 48 126 | 11/1996 |
| DE | 197 44 481 | 10/1997 |
| DE | 197 44 485 | 10/1997 |
| DE | 102 04 941 | 2/2002 |
| DE | 102 30 475 | 7/2002 |
| DE | 102 36 515 | 8/2002 |
| EP | 1 053 671 | 3/2000 |
| WO | WO 89/10548 | 4/1989 |
| WO | WO 99/40419 | 8/1999 |
| WO | WO 99/46971 | 9/1999 |
| WO | WO 00/00818 | 1/2000 |
| WO | WO 01/35076 | 5/2001 |

OTHER PUBLICATIONS

Patent Abstracts of Japan, JP-57104848 A, Dec. 22, 1980, 1 Page.
A Rugged Near-Infrared Spectrometer For The Real-Time Management of Grains During Harvest, Jun. 2000, Chas. W. von Rosenberg Jr., Agostino Abbate and Jessica Drake, 5 Pages.

* cited by examiner

*Primary Examiner*—David Porta
*Assistant Examiner*—Yara B Green

(57) ABSTRACT

A measurement device for detecting agricultural crops located within a conveyor channel. The measurement device includes a light-transmitting panel positioned adjacent to the conveyor channel and is configured to be movable between an operational position and a cleaning position. The measurement device includes a sensor positioned with respect to the light-transmitting panel so as to detect the agricultural crops in the conveyor channel through the light-transmitting panel. A harvesting machine is particularly adapted to utilize the measurement device.

17 Claims, 1 Drawing Sheet

AGRICULTURAL MEASUREMENT DEVICE WITH MOVABLE DETECTOR HEAD

BACKGROUND

1. Field of the Invention

The invention generally concerns a measurement device with a sensor for capturing the contents and/or characteristics of components of agricultural crops.

2. Related Technology

Measurement devices suitable for analyzing the contents of organic material comprise, as a rule, sensors that work with light in the near-infrared wavelength rate in a reflection (NIR) or transmission (NIT) mode and are provided with light sources and optical analyzers. Several kinds of measurements devices of these types have been recommended for application to harvesting machines in order to capture and document the characteristics of the crop.

Harvesting machines with these kinds of measurement devices have been described, for example, in WO 99/46974 A, WO 99/40419 A, WO 00/00818 A, EP 1 053 671 A, and in C. von Rosenberg et al: "A Rugged Near-infrared Spectrometer for the Real-time Measurement of Grains during Harvest," *Spectroscopy* 15/6 (2000). The measurement devices are each arranged near a conveyor channel of the harvesting machine, through which the crop flows or is conveyed. In DE 012 36 515 C, a measurement device of this kind is applied to the wall of a chamber that is filled with a crop sample taken from the main crop flow by screw conveyor.

In the known measurement devices, a window having a transparent pane is arranged between the actual measurement device and the crop flow to permit light to travel through the window and to prevent the crop from doing the same and passing into the interior of the measurement device. The pane is arranged, as a rule, so as to be level with the wall of the conveyor channel. Under certain conditions, this positioning has the disadvantage that the pane becomes dirty from adhering crop or other impurities, such as dust or debris, so that optical measurement of the crop can no longer occur because the pane is obstructed by crop or other debris adhered thereto. For example, the dust or debris may prevent reflection and/or reception of the sensor transmission. As another example, the crop adhered to the pane may cause false or misleading readings, particularly if the crop adhered to the pane is different from the crop moving below.

In WO 00/00818 A, the pane is inclined in one embodiment at an angle of 5 to 10° with respect to the surface of the measurement device and the conveyor channel and protrudes somewhat beyond the surface of the measurement device into the conveyor channel. Through this angle, it is intended to achieve that light from the light source of the measurement device that passes through and is reflected by the pane does not arrive at the detector. The pane is arranged so as to be stationary and impurities can accumulate on the pane. In an embodiment in which the pane protrudes permanently into the crop flow, a strong wear occurs on the pane through the constant contact with the crop flow, if a special wear-resistant material is not used.

The problem of impurities on the sensor surface is also present in sensors that do not work optically. Thus, a measurement chamber is recommended in DE 197 44 485 A in which the crop is studied by a capacitive sensor that captures moisture, through which a movable element is forced to be emptied and cleaned. In DE 197 44 481 A, it is recommended that the sensor be applied to the wall of a screw conveyor to the conveyor windings of which cleaning elements are applied. JP 57 014 848 A describes a sensor for capturing grain moisture that captures the conductivity of grains arranged by means of two electrodes arranged in a conveyor channel. One of the electrodes is moved before and after a measurement, in order to create contact between the grains adhering to the electrode and the grains in the conveyor channel, and the electrodes are thereby cleaned. These solutions are not suitable, however, for sensors whose sensitive surfaces are arranged on the wall of a conveyor channel in which the crop is not transported by a separate conveyor, but only accelerated at the start of the conveyor channel by blowing or something similar.

SUMMARY OF THE INVENTION

In one aspect of the invention, a measurement device is provided that reduces or prevents the disadvantageous effects of crops accumulating on a sensitive surface of a sensor. The measurement device includes a light-transmitting panel positioned adjacent to the conveyor channel and a sensor positioned with respect to the light-transmitting panel so as to detect the agricultural crops in the conveyor channel through the light-transmitting panel. The light-transmitting panel is movable between a first position and a second position. In the first position, the light transmitting panel is flush with the wall surfaces defining the conveyor channel and measuring of the crop therein is performed. While in the second position, the light-transmitting panel extends into the conveyor channel so that the agricultural crops are able to contact at least a portion of the light-transmitting panel, thereby cleaning the panel and removing debris therefrom.

This configuration potentially reduces possible sensor transmission failures and falsifications of the measurement results. Output values of the sensor can be charted with reference to the ground and/or applied to regulate or set the working parameters of the harvesting machine. In a preferred embodiment, the sensor can be moved together with the surface between the first and second position to avoid changes in the relative positions of sensor and light-transmitting panel that could lead to measurement errors.

It is preferred to mount the surface, and advantageously also the sensor, at its or their end(s) lying in the direction of flow of the crop in the conveyor channel so as to rotate about an axis that extends perpendicular to the direction of flow. At the end(s) that lie(s) upstream from the flow direction, the surface, and advantageously also the sensor, is/are connected to the wall of the conveyor channel so as to be movable manually or by an activator, in order for the surface and/or the sensor to rotate about the axis and move between the first and second positions.

The device is appropriately driven to the second position by an activator that is activated by an outside force on a manual input from an operator or automatically. The device can be driven to the second position after the end of a certain time interval (e.g. after 10 minutes) or automatically after an implausible output value is detected from the sensor. An implausible output value of this kind exists, for example, when the output value of the sensor is constant for a certain time interval (e.g. 10 seconds) or when existence of crop is indicated when no crop is flowing through the conveyor channel, which can be shown by means of the operating state of the conveyor elements or by other sensors, e.g. a light beam. In a similar way, i.e. after the end of a certain time interval or by changing values of the sensor, the surface and possibly the sensor can be brought automatically into the first position.

It is advantageous for the sensor to work optically, especially in the near-infrared range, and especially in the reflection mode. The surface is then a pane that is transparent to the wavelength range used by the sensor. This pane consists advantageously of a relatively hard, wear-resistant material, diamond or sapphire glass. In other embodiments, the sensor can also work capacitatively or with microwaves or it can measure the electric resistance of the crop in order to determine its moisture.

The measurement device according to the invention can be used in stationary systems or on any harvesting machine in which the crop flows past a sensor or the sensor is moved past the crop, e.g. on a swath.

Further objects, features and advantages of this invention will become readily apparent to persons skilled in the art after a review of the following description, with reference to the drawings and claims that are appended to and form a part of this specification.

BRIEF DESCRIPTION OF THE DRAWINGS

In the drawings below, two embodiments of the invention are described in more detail.

DETAILED DESCRIPTION OF THE INVENTION

Figure 1:
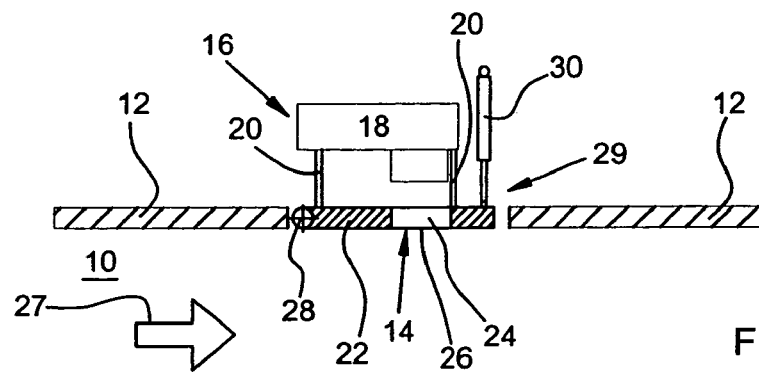
FIG. 1 shows a schematic side view of a first embodiment of a measurement device in its first position.

In the drawings, a conveyor channel of an automatic harvesting machine is shown by reference number 10, whereby this can involve, for example, a movable discharge device on a field chaff-cutter for sending chopped crop onto a vehicle according to the set ejection direction, the input channel of a ball press, or a region of a mowing thresher, in which threshed or unthreshed grain is conveyed, such as an inclined conveyer or a conveyor for filling the grain tank. The conveyor channel 10 is bordered by wall 12. The other walls of the conveyor channel 10 are omitted from the figures. In FIGS. 1 through 4, the crop in the harvesting operation moves horizontally through the conveyor channel 10 from left to right in the direction generally indicated by arrow 27.

In the wall 12, an opening 14 is provided, which serves to accept a measurement device, which is generally indicated by reference numeral 16. The measurement device 16 comprises, in both embodiments, a sensor 18, which is an optical sensor operating in the reflection mode. The sensor 18 operates in the near-infrared range and applies broadband light to the crop in the conveyor channel 10 and separates the light reflected by the plants through wavelength-dispersion elements (grid, etc.) into a spectrum, which is detected by suitable light-sensitive detectors. A suitable sensor is described in U.S. Pat. No. 6,421,990, the content of which is incorporated into the present document by reference.

The sensor 18 captures several properties of the chopped plants, especially their components and one or more qualities derived from them. For example properties in the crop are captured by the sensor 18 include organic contents, such as starch, enzyme-soluble organic substances (ElosT), oil, and raw protein. In addition, the content of inorganic components, such as minerals (ash), e.g., sodium and magnesium, impurities in the form of sand (silicon dioxide), and earth or water, and the color of the plants are measured.

Parameters of the crop that can be captured in addition or alternatively to the components or that can be derived from the components include the dry-matter content, the fiber length, the digestibility, the energy content, and the raw-fiber content of the crop. The raw-fiber content, and the fiber length in particular, can be determined by further processing the output signals from the sensor by means of a computer.

The sensor 18 is connected to a holding plate 22 by one or more carrier arms 20. The holding plate 22 carries a pane 24 with an outer surface 26 facing the crop flow. Through the pane 24, the light generated by the sensor 18 reaches the crop and the light reflected by the crop returns to the sensor 18, which detects it. A support of the sensor 18, which contains an optical element, extends in the direction of the pane 24 and could also lie next to the pane 24 and/or the holding plate 22 to screen outside light.

Figure 2:
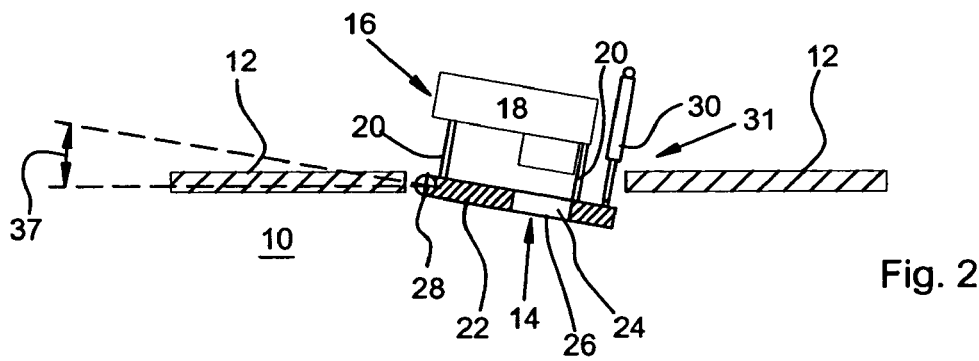
FIG. 2 shows a schematic side view of the first embodiment of the measurement device in its second position.

The holding plate 22, is mounted at its upstream end (in the direction 27 of flow of the crop in the conveyor channel 10, i.e. and the left end in FIGS. 1 and 2) so as to rotate about an axis 28 perpendicular to the flow direction of the crop and extending in the plane of the wall 12. On the holding plate 22, at its downstream end in the direction of the crop flow, i.e., on its right end in FIGS. 1 and 2, an activator 30 is mounted in the form of a hydraulic cylinder or an electric linear motor. The other end of the activator 30 is mounted in turn on an element (not shown) that is coupled mechanically to the wall 12 or fixed portion of the machine.

By activating the activator 30, the holding plate 22, and with it the pane 26 and the sensor 18, can be rotated about the axis 28 to an angle 37 with respect to the direction 27 of the flow of the crop. For example, the holding plate 22 is connected to a hinge device configured to pivot about the axis 28. The angle 37 is preferably an acute angle, and is more preferably between 5 and 15 degrees. Thereby, the holding plate 22 can be brought from its first position 29 to its second position 31. Its first position, shown in FIG. 1, serves for normal measurement operation and is the position in which the holding plate 22 and with it the surface 26 extend parallel to the adjacent wall 12. The second position 31, shown in FIG. 2, is inclined with respect crop flow. In the second position 31, the crop contacts the surface 26 of the pane 24 at a certain acute angle and leads to an improvement in measurement precision. For example, the crop contacts the outer surface 26 in a wiping motion and removes dust and other debris (such as crop fragments) from the panel 24. In order to prevent excessive wear, the pane 24 is preferably made of diamond or sapphire glass.

The activator 30 is activated to move the measurement device 16 downwards into the second position 31 by manual input from an operator or automatically when a certain time interval has ended or the signals from the sensor 18 remain constant for a certain time interval or indicate that the crop is present although it can be recognized from the state of other sensors or activators that in fact no crop is being conveyed. The measurement device 16 is actuated upwards to the first position 29 in a similar way.

Figure 3:
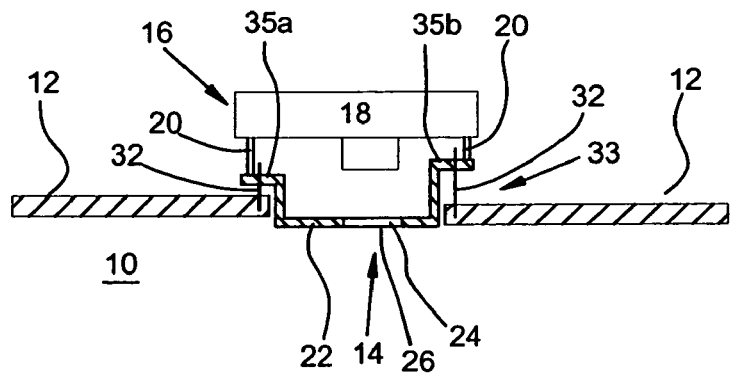
FIG. 3 shows a schematic side view of a second embodiment of the measurement device in its first position.
Figure 4:
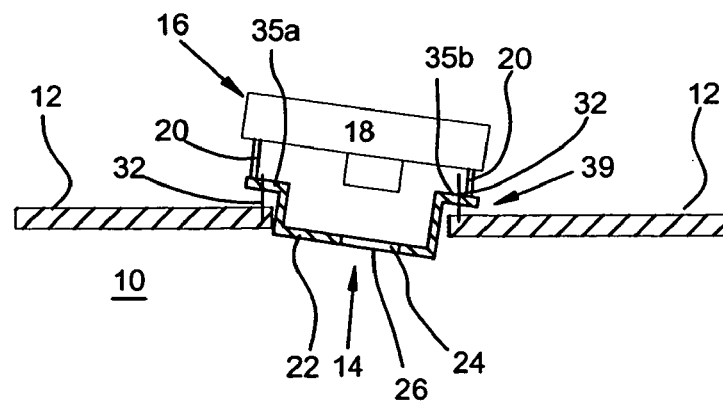
FIG. 4 shows a schematic side view of the second embodiment of the measurement device in its second position.

The second embodiment, shown in FIGS. 3 and 4, corresponds to the first embodiment in its essential parts. Equivalent components are therefore identified with the same reference numbers. In contrast to it, however, the holding plate 22 is formed, cross-sectionally, in a U shape, and the upstream end and the downstream end are both connected to the wall 12 through an activator 32 in the form of a set screw. By manually activating the set screws 32, the holding plate 22, with the sensor 18 and the pane 24, can be moved between the first position 33, shown in FIG. 3, in which the surface 26 extends parallel to the adjacent wall 12 for normal operation, and the second position 39, shown in FIG. 4, in which the surface 26 extends at an angle to the crop flow and it is cleaned of any impurities via contact by the crop, as described above with respect to the design shown in FIGS. 1 and 2.

The set screws 32 shown in the figures are both configured to independently adjust the position of the measurement device 16 to improve the range of movement thereof. More specifically, each side of the measurement device 16 is able to move independently from the other side to permit a wide range of operating positions. Alternatively, the upstream set screw 32 does not permit vertical adjustment of the upstream side of the holding plate 22 and the downstream set screw does permit such adjustment of the downstream side of the holding plate 22, thereby permitting the holding plate 22 to pivot about the contact with the upstream set screw.

The U-shaped holding plate 22 includes a flange portion 35a, 35b on each side thereof to receive the set screws. Additionally, the downstream flange portion 35b is spaced a larger (vertical in the figures) distance from the pane 24 than the upstream flange portion 35a is spaced therefrom to permit the pivoting movement of the holding plate 22.

It is therefore intended that the foregoing detailed description be regarded as illustrative rather than limiting, and that it be understood that it is the following claims, including all equivalents, that are intended to define the spirit and scope of this invention.

The invention claimed is:

1. A measurement device for detecting agricultural crops, the measurement device comprising:
a wall defining a portion of a conveyor channel for conducting a flow of said crops in a first direction and being provided with a first opening;
a holding plate being positioned within said first opening and being provided with a second opening;
a light-transmitting panel being positioned within said second opening; and
an optical sensor capable of generating a light source and of receiving reflected light being positioned with respect to the light-transmitting panel so as to impinge generated light upon, and to receive reflected light from, the agricultural crops in the conveyor channel and thereby detect the agricultural crops in the conveyor channel through the light-transmitting panel; and
said holding plate, together with said light-transmitting panel, being mounted for movement between a first position and a second position, and, while in the second position, the light-transmitting panel extending in a second direction at least partly beyond said wall into the conveyor channel in oblique relationship to said first direction so that agricultural crops passing through said channel are able to contact and clean at least a portion of the light-transmitting panel.

2. The measurement device as in claim 1, wherein said light-transmitting panel, while said holding plate is in the first position, is substantially flush with a portion of the wall.

3. The measurement device as in claim 1, wherein said second direction forms an acute angle with the first direction.

4. The measurement device as in claim 3, wherein the acute angle is between 5 and 15 degrees.

5. The measurement device as in claim 1, wherein the sensor is coupled to said holding plate so as to be movable along with the light-transmitting panel.

6. The measurement device as in claim 1, wherein said holding plate forms a hinge connection with said wall at said opening and thereby pivotally connects the light-transmitting pane to the wall.

7. The measurement device as in claim 6, wherein the pivotable hinge is located on an upstream side of the light-transmitting panel.

8. The measurement device for detecting agricultural crops, as defined in claim 1, and further including
an adjustable height connector connecting the light-transmitting panel to the wall for moving said light-transmitting panel between said first and second positions.

9. The measurement device as in claim 8, further comprising a second adjustable-height connector connecting the light-transmitting panel to the wall with said second adjustable-height connector being adjustable relative to the first mentioned adjustable height connector so as to effect said oblique relationship of said light-transmitting panel.

10. The measurement device for detecting agricultural crops, as defined in claim 1, and further including
an activator coupling the light-transmitting panel to the wall and configured to move the light-transmitting panel between the first and second positions.

11. The measurement device as in claim 10, wherein the activator is manually-operated.

12. The measurement device as in claim 10, wherein the activator is automatically-operated.

13. The measurement device as in claim 12, wherein the activator is configured to move the light-transmitting panel into the second position after a predetermined amount of time.

14. The measurement device as in claim 1, wherein the light-transmitting panel is made of a wear-resistant material.

15. The measurement device as in claim 14, wherein the wear-resistant material includes a material selected from the following group consisting of diamond and sapphire.

16. The measurement device as in claim 1, wherein the sensor is configured to detect properties of agricultural crops.

17. A harvesting machine for harvesting agricultural crops, the harvesting machine comprising:
a wall defining a portion of a conveyor channel for transporting the agricultural crops and containing an opening; and
a measurement device for detecting the agricultural crops being mounted to the wall, the measurement device including:
a light-transmitting panel positioned at least approximately within said opening of said wall of the conveyor channel; and
an optical sensor having the capability of generating a source of light and for receiving reflected light being positioned with respect to the light-transmitting panel such that generated light passes through said panel and impinges upon agricultural crops in the conveyor channel, and such that light reflected from said crops pass back through said panel and are received by said sensor, thereby detecting the agricultural crops in the conveyor channel through the light transmitting panel; and
said light-transmitting panel being mounted to the wall for movement between a first position and a second position, and while in the second position the light-transmitting panel extending into the conveyor channel so as to be oriented obliquely to a direction of travel of the agricultural crops through said conveyor channel so that the agricultural crops are able to contact and clean at least a portion of the light-transmitting panel.

* * * * *